(12) United States Patent
Shahbazpour et al.

(10) Patent No.: US 7,063,086 B2
(45) Date of Patent: Jun. 20, 2006

(54) BREATHING ASSISTANCE APPARATUS

(75) Inventors: Mehdi Shahbazpour, Auckland (NZ); Michael John Blood Trousdell, Auckland (NZ); Chris Earl Nightingale, Auckland (NZ); Alastair Edwin McAuley, Auckland (NZ); Aidan Mark Shotbolt, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 500 days.

(21) Appl. No.: 10/237,833

(22) Filed: Sep. 9, 2002

(65) Prior Publication Data

US 2003/0066530 A1  Apr. 10, 2003

Related U.S. Application Data

(63) Continuation-in-part of application No. 09/662,203, filed on Sep. 14, 2000.

(30) Foreign Application Priority Data

Sep. 23, 1999 (NZ) .................... 337993
Sep. 13, 2001 (NZ) .................... 514186

(51) Int. Cl.
A62B 9/02 (2006.01)

(52) U.S. Cl. .................... 128/205.24; 128/204.18; 128/207.16

(58) Field of Classification Search .......... 128/200.24, 128/205.24, 207.14–207.18; 251/12, 142, 251/149, 175, 176, 180, 283, 304, 313, 321, 251/337; 137/484.2

See application file for complete search history.

(56) References Cited

U.S. PATENT DOCUMENTS

| 2,483,722 | A | * | 10/1949 | Bennett | ...................... 137/102 |
| 3,618,861 | A | * | 11/1971 | Holmes | ................. 239/265.27 |
| 4,088,131 | A | | 5/1978 | Elam et al. | |
| 4,224,939 | A | | 9/1980 | Lang | |
| 4,655,213 | A | | 4/1987 | Rapoport et al. | |
| 4,658,213 | A | | 4/1987 | Finley | |
| 5,065,756 | A | | 11/1991 | Rapoport | |
| 5,163,424 | A | | 11/1992 | Kohnke | |
| 5,398,673 | A | | 3/1995 | Lambert | |
| 5,538,002 | A | | 7/1996 | Boussignac et al. | |
| 5,584,288 | A | | 12/1996 | Baldwin | |
| 5,630,411 | A | * | 5/1997 | Holscher | ............... 128/205.24 |
| 5,657,752 | A | | 8/1997 | Landis et al. | |
| 5,803,065 | A | | 9/1998 | Zdrojkowski et al. | |
| 5,813,401 | A | * | 9/1998 | Radcliff et al. | ........ 128/205.24 |
| 6,615,831 | B1 | * | 9/2003 | Tuitt et al. | ............. 128/204.18 |
| 6,739,338 | B1 | * | 5/2004 | Tanhehco et al. | ...... 128/205.24 |
| 6,772,754 | B1 | * | 8/2004 | Mendenhall | ........... 128/200.14 |

FOREIGN PATENT DOCUMENTS

GB  1238649  7/1971

* cited by examiner

Primary Examiner—Glenn K. Dawson
(74) Attorney, Agent, or Firm—Trexler, Bushnell, Giangiorgi, Blackstone & Marr, Ltd.

(57) ABSTRACT

A valve for use in a CPAP system or any stem at a pressure above ambient which vents the pressurised gases from the blower during expiration. Due to the pressure-flow characteristics of the blower this results in the patient having a much lower airway pressure during expiration making breathing easier. The valve includes a movable member which blocks flow from the blower to the patient during exhalation and vents externally. During inhalation gases flow normally from the blower to the patient. Also disclosed is a further application as an antiasphyxia.

11 Claims, 8 Drawing Sheets

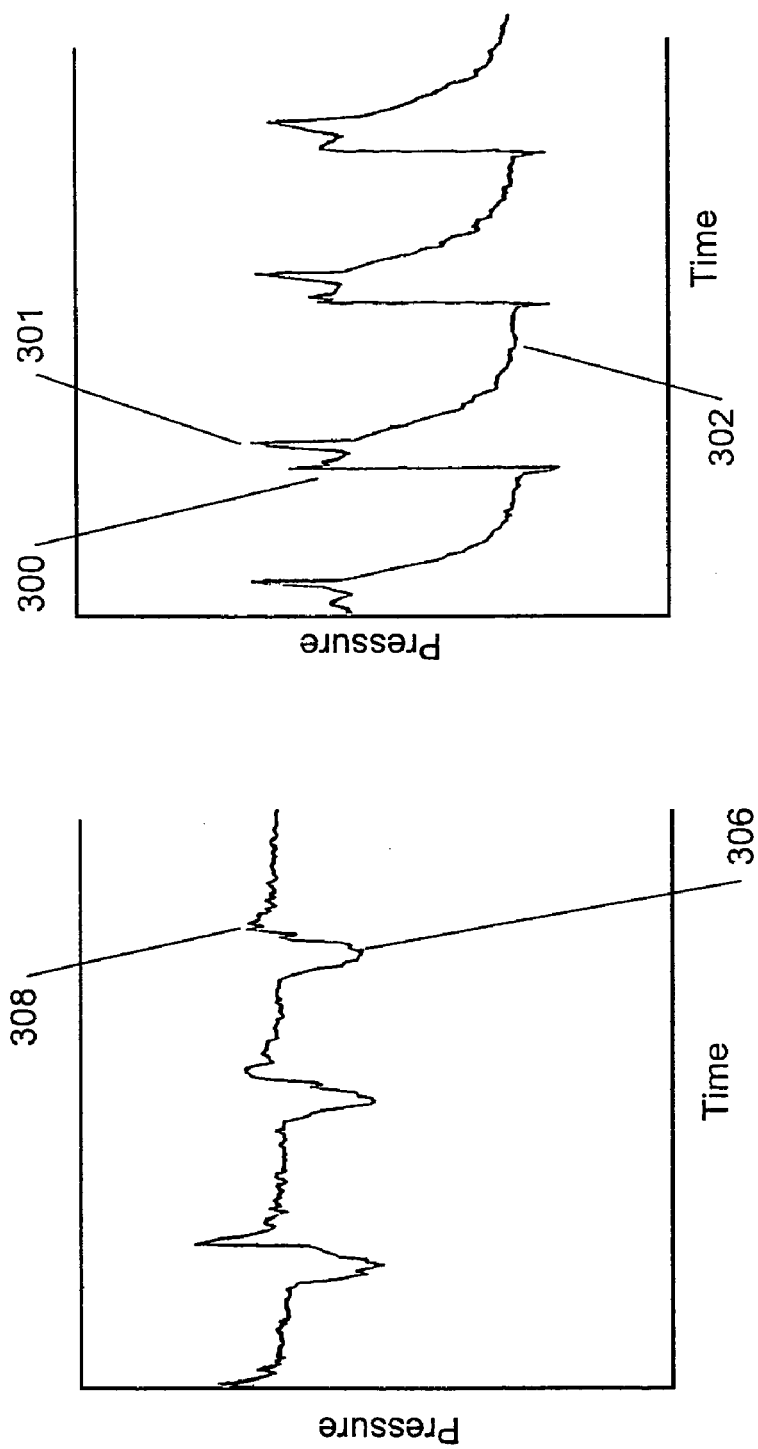

BREATHING ASSISTANCE APPARATUS

This application is a Continuation-In-Part of U.S. patent application Ser. No. 09/662,203, filed on Sep. 14, 2000.

FIELD OF INVENTION

This invention relates to valves particularly through not solely for inclusion in the breathing circuit of a respirator.

SUMMARY OF THE PRIOR ART

A medical breathing circuit such as might be used in a Continuous Positive Airway Pressure Respirator (CPAP) includes an inspiratory gases tube which has one end thereof connected to the patient through an interface. For example through an endotracheal breathing tube extending into the trachea and ending just above the lungs. The other end thereof is connected to a respirator providing pressurised gases. The connection to the respirator may be direct or a self contained humidifier may be interposed.

One disadvantage of CPAP treatment is that it effectively reverses the normal breathing function. The patient has to relax to breath in and requires effort to breath out. Since normal breathing requires the exact opposite, the use of CPAP is sometimes difficult initially.

A number of devices exist to reduce the effort required by the patient to exhale. For example U.S. Pat. No. 5,657,752 assigned to Airways Associates describes a variable orifice venting aperture member in the nasal mask to help vent the exhalations. U.S. Pat. No. 5,065,756 assigned to New York University includes vent holes in the face mask for rapid discharge of exhaled air. U.S. Pat. No. 4,658,213 assigned to New York University includes a threshold valve to release air from the mask. Alternatively electronic methods exist such as that described in U.S. Pat. No. 5,803,065 assigned to Respironics have been used to improve the effectiveness of CPAP therapy.

Our Australian Patent Application No. 56596/00 describes a valve for use in a CPAP system or any stem at a pressure above ambient which vents the pressurised gases from the blower during expiration. Due to the pressure-flow characteristics of the blower this results in the patient having a much lower airway pressure during expiration making breathing easier. The valve includes an axially movable member which blocks flow from the blower to the patient during exhalation and vents externally. During inhalation gases flow normally from the blower to the patient.

However to some degree these existing devices are still somewhat ineffective. Also in some cases these apparatus include a bulky face mask and strapping which may be uncomfortable for the user.

In International Patent Application No. PCT/AU99/001169 an antiasphyxia valve is described including a flap which operates when the difference between the inner pressure and the outside pressure drops below a threshold for example when the ventilator fails.

SUMMARY OF THE INVENTION

It is an object of the present invention to provide a valve for a respiratory breathing circuit which will obviate the above disadvantage or will at least provide healthcare providers with a useful choice.

Accordingly in a first aspect the invention may broadly be said to consist in a device for controlling gas flow between a pressurised gases supply and a user, comprising:

a body portion including a first opening adapted to be in fluid communication with a pressurised gases supply, a second opening adapted to be in fluid communication with a user, and an interior fluidally communicating said first opening with said second opening at least one auxiliary outlet in said body portion, and valve means configured to close said outlet when said gas flow through said interior is above a predetermined threshold.

Preferably said valve means configured to fluidally communicate said outlet with said first opening and said second opening when said gas flow is below said predetermined threshold.

Preferably said valve means comprises a helically or rotatably moveable member configured to substantially seal inside said body portion but in use helically or rotatably moveable therein.

Preferably said moveable member includes at least one vane, said vane adapted to impart a helical or rotational force on said moveable member, accordingly to said gas flow biasing means restraining said rotation and at least one aperture adapted to communicate said outlet with said interior when said gas flow below said threshold close to said outlet when said gas flow above said threshold.

Preferably said biasing means and said vane configured such that said threshold is between said gas flow during inhalator and said gas flow during exhalation of said user.

Alternatively said biasing means and said vane configured such that said threshold is below said gas flow during inhalation and exhalation of said user.

Preferably said at least one vane comprises four angled vanes.

Alternatively said at least one vane comprises three angled vanes.

Preferably said biasing means comprises a forsilnal spring connected between said moveable member and said body portion.

Preferably said biasing means comprise at least one magnet in said movable member or said body portion interacting with a magnetic material is said body portion or said moveable member respectively.

In a second aspect the present invention consists in a system for supplying gases to a user at a pressure above ambient comprising:

a pressurised gases supply, gases delivery means for supplying said gases to said user in fluid communication with said pressurised gases supply and said user, and flow control means disposed within said gases delivery means or in fluid communication therewith, said flow control means comprising a device according to any one of the preceding claims.

Preferably a system further comprising humidification means, for humidifying said gases before delivery to said user, disposed within or in fluid communication with said gases delivery means.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the forgoing and also envisages constructions of which he following gives examples.

BRIEF DESCRIPTION OF THE DRAWINGS

One preferred form of the present invention will now be described with reference to the accompanying drawings in which;

FIG. 7 is a graph illustrating the typical pressure profile experienced by a patient according to traditional CPAP methods, FIG. 8 is a graph illustrating the typical pressure profile experienced by a patient according to the preferred embodiment of the present invention.

DETAILED DESCRIPTION OF THE PREFERRED EMBODIMENTS

The present invention attempts to provide a simple to manufacture device which attempts to improve comfort levels for a user undergoing CPAP therapy. This is done by providing a three-way valve in the conduit between the respirator and the patient which allows both gases to flow to the patient and exhalations to be expelled to flow through the same conduit. This makes exhaling easier for the user, without the need for additional apparatus to be worn by the user. If the gases supplied to the user are to be humidified, the valve is positioned between the respirator and the humidifier, i.e. upstream of the humidifier. The contents of copending U.S. application Ser. No. 09/662203 are incorporated herein by reference.

Figure 1:
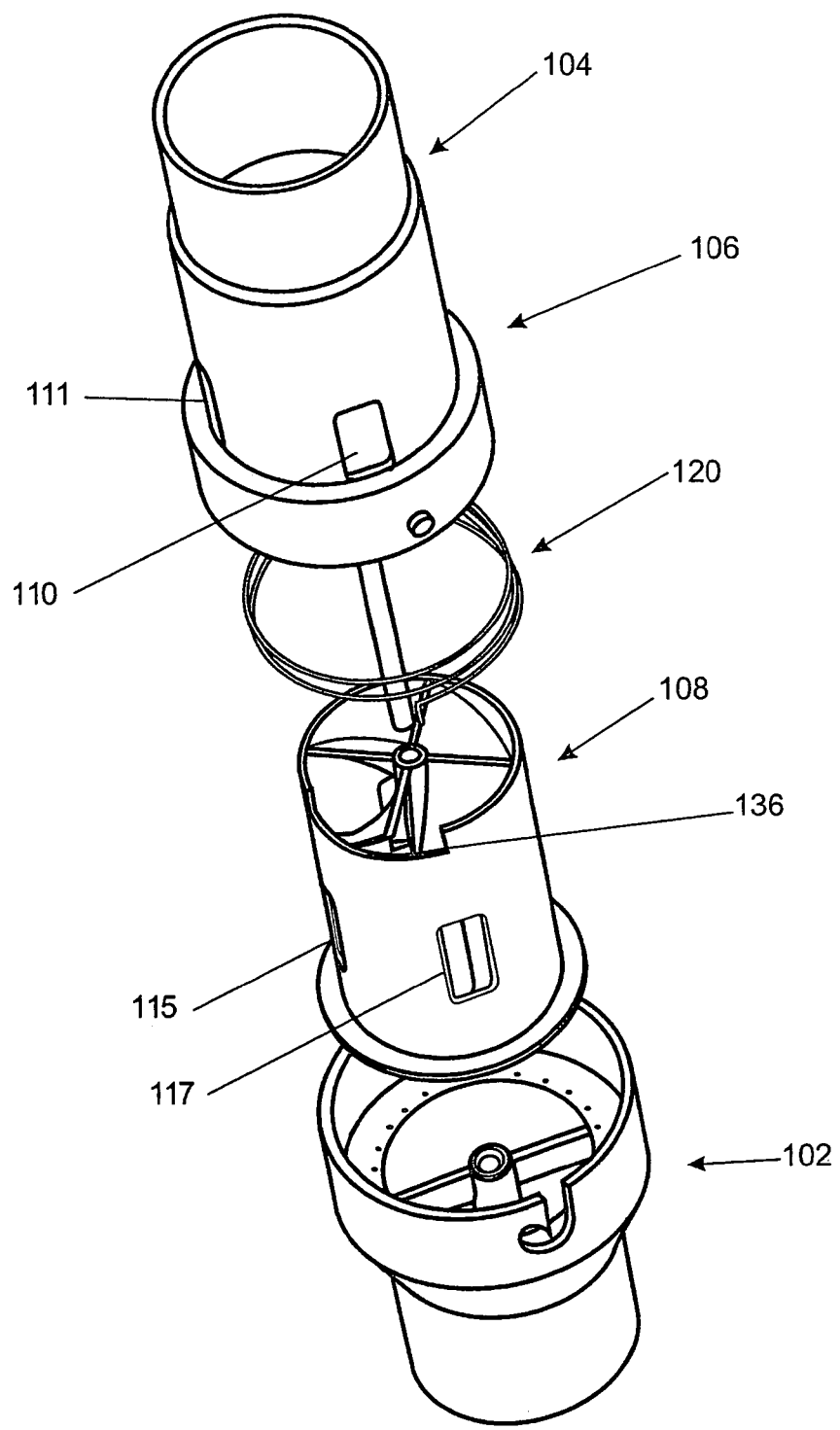
FIG. 1 is a blown out perspective of the present invention, showing the components that fit together to form the valve.

Referring now to FIG. 1, we see the valve in more detail. The valve body 100 has two ends 102, 104 adapted for connection to a typical respiratory conduit and an enlarged centre section 106 which houses the rotatably moveable valve member 108. The centre section 106 includes four apertures 110, 111, 112, 113 on its periphery, located evenly spaced around an imaginary central point.

The valve member 108 is of a generally hollow cylindrical construction and includes four matching apertures 114, 115, 116, 117 on its periphery again located evenly spaced around an imaginary centre point. Also part of the valve member 108 is a set of vanes 118 which join to the inner periphery of the valve member. The vane design has an initial angle of 0 degrees so that there is no separation of the flow and a final angle of 60 degrees at the end to of the vane. So the profile of the vane taken at any radius would be a circular curve, of 60 degrees. Thus when gas flows from the inlet 119 to the outlet 121 the action of the vanes causes an anticlockwise force (looking from above the outlet) on the movable member 108. This force is restricted by inhalatory stops 135 at which point the apertures do not match and no gases are vented externally.

Figure 2:
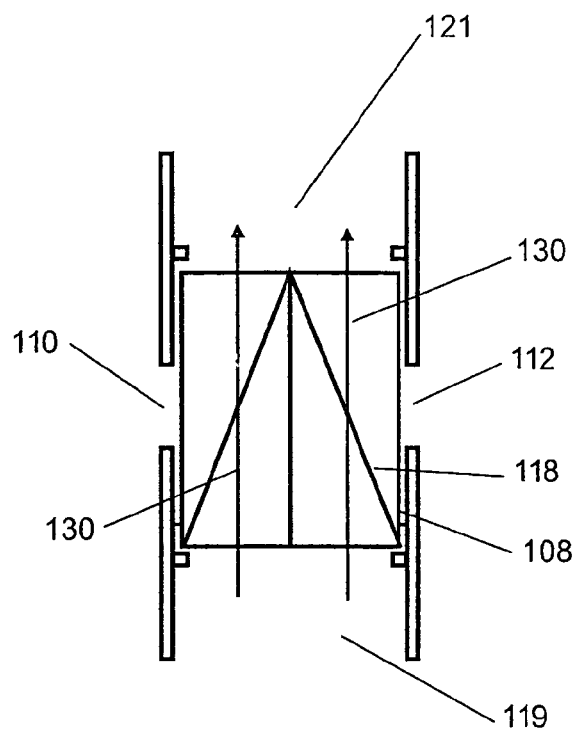
FIG. 2 is a side sectional view of the present invention during inhalation.
Figure 3:
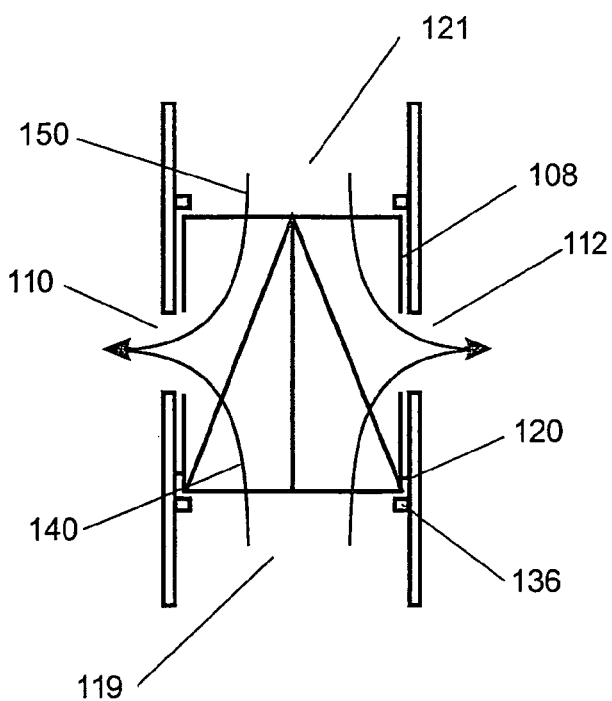
FIG. 3 is a side sectional view of the present invention during exhalation.

Referring now to FIGS. 2 and 3, the operation of the valve is now explained. During a patient inhalation the valve member is in the open position as shown in FIG. 2. The gas flow is as designated by arrow 130, flows from inlet 119 over the vanes 118 and out outlet 121, which forces the movable member 108 to rotate anti-clockwise in FIG. 2. The apertures in the body portion 110, 111, 112, 113 in this position are closed off and do not match up with the apertures in the valve member 114, 115, 116, 117. In this case the valve provides low resistance from the respirator to the patient.

When the patient exhales, shown in FIG. 3, back pressure on the patient side reduces or stops the flow through the valve. A helical or coil spring 120 connected to the valve member imparts a clockwise force. This (in the absence of anticlockwise force on the vane) forces the valve member 108 to rotate clockwise, until it hits the expiratory stops 136. Once forced to this position, the apertures 110, 111, 112, 113 in the body portion and the apertures in the valve member 114, 115, 116, 117 align. This means that gases from the respirator through inlet 119 are discharged into the atmosphere, shown by arrow 140 and the exhalatory gases from the patient through outlet 121, shown by arrow 150, are also discharged into the atmosphere.

Figure 4:
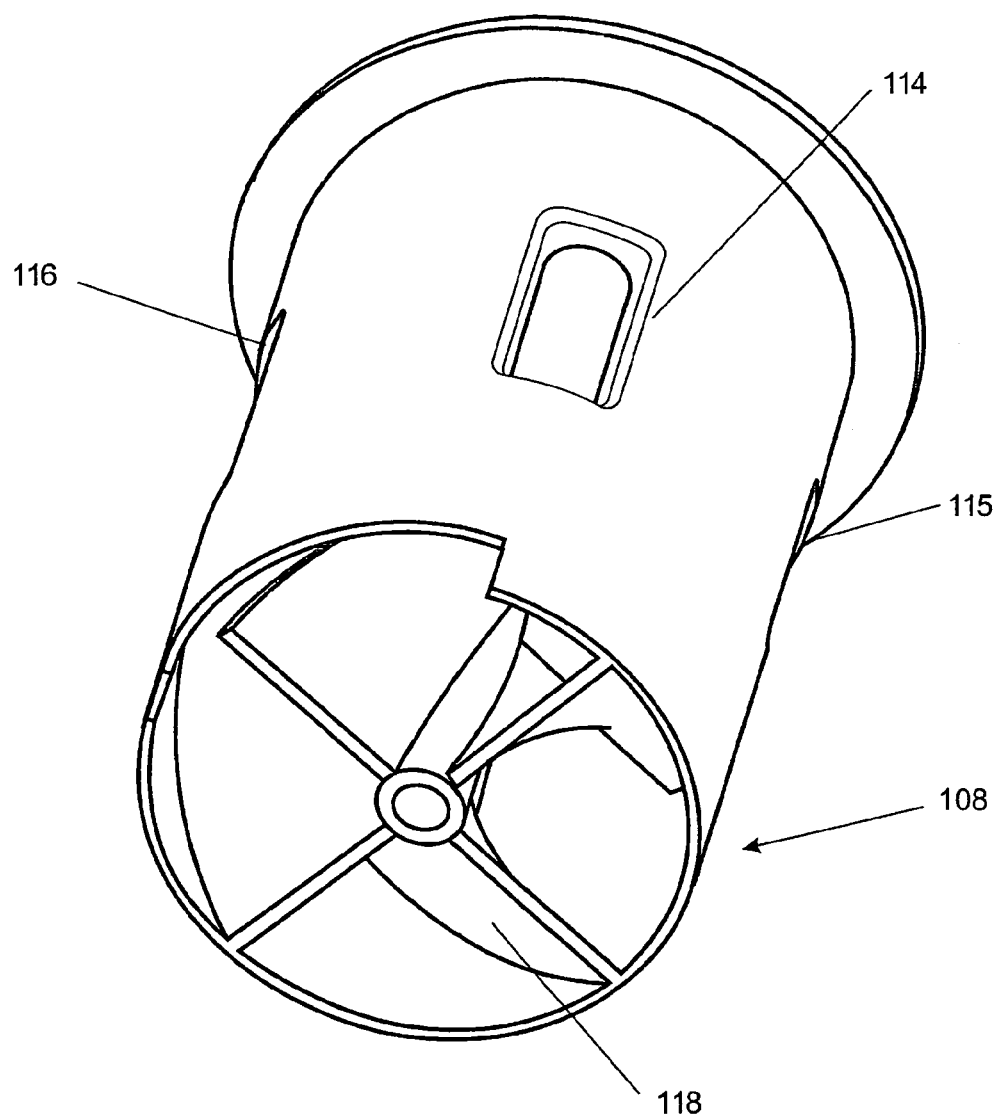
FIG. 4 is a perspective view of the valve member.

Helical spring preferably has a spring constant in the range of 2–3 cm-g torque. This means that the back pressure that the patient experiences while exhaling is much reduced due to the typical pressure flow rate characteristics of the respirator shown in FIG. 4. During inhalation the respirator might operate at point 200. Whereas during exhalation, due to the high flow rate through aperture 110 into the atmosphere, operation might be at point 202 with correspondingly low pressure seen by the patient.

Each of the valve body portion 102, 104 and valve member 108 may be simply manufactured by injection moulding, for example a polycarbonate plastics material or other suitable plastics material.

Figure 5:
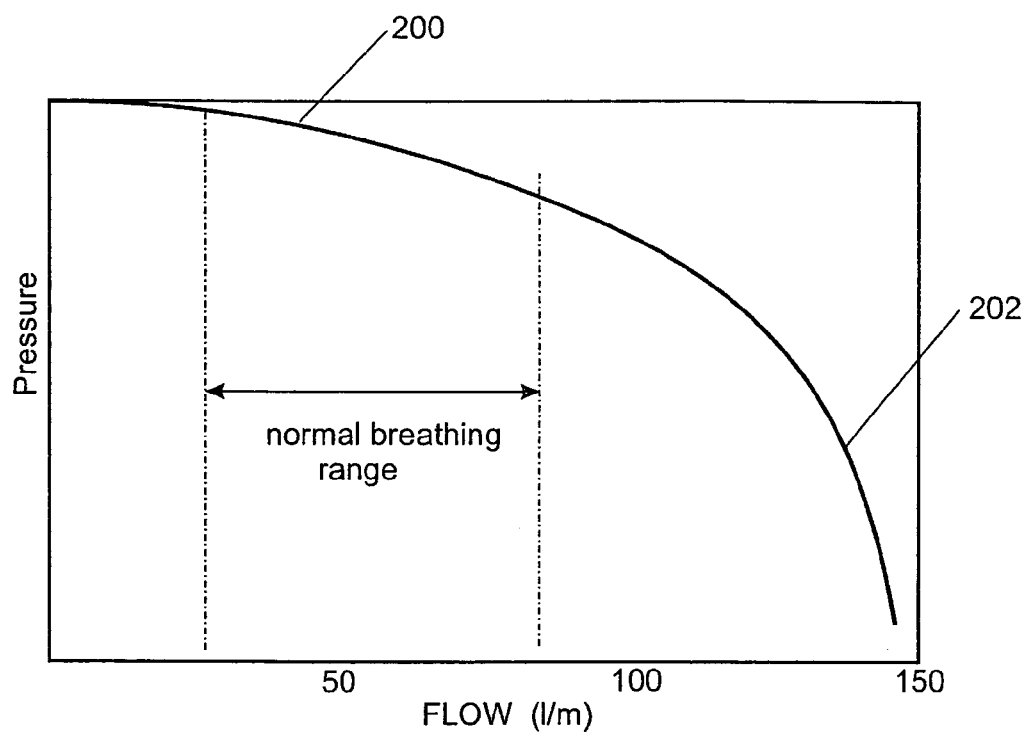
FIG. 5 is a graph of a typical pressure/flow rate characteristics of a respirator.

A typical respiratory humidification circuit such as might employ the present invention is shown diagrammatically in FIG. 5, and includes the respirator 230, humidifier 231, and the associated respiratory breathing tubes 233 and 234. A patient 236 under treatment is shown connected to the system. As indicated in FIG. 5 the valve of the present invention is connected between the humidifier 231 and the outlet port of the respirator 230 and is indicated by reference numeral 237.

Figure 6:
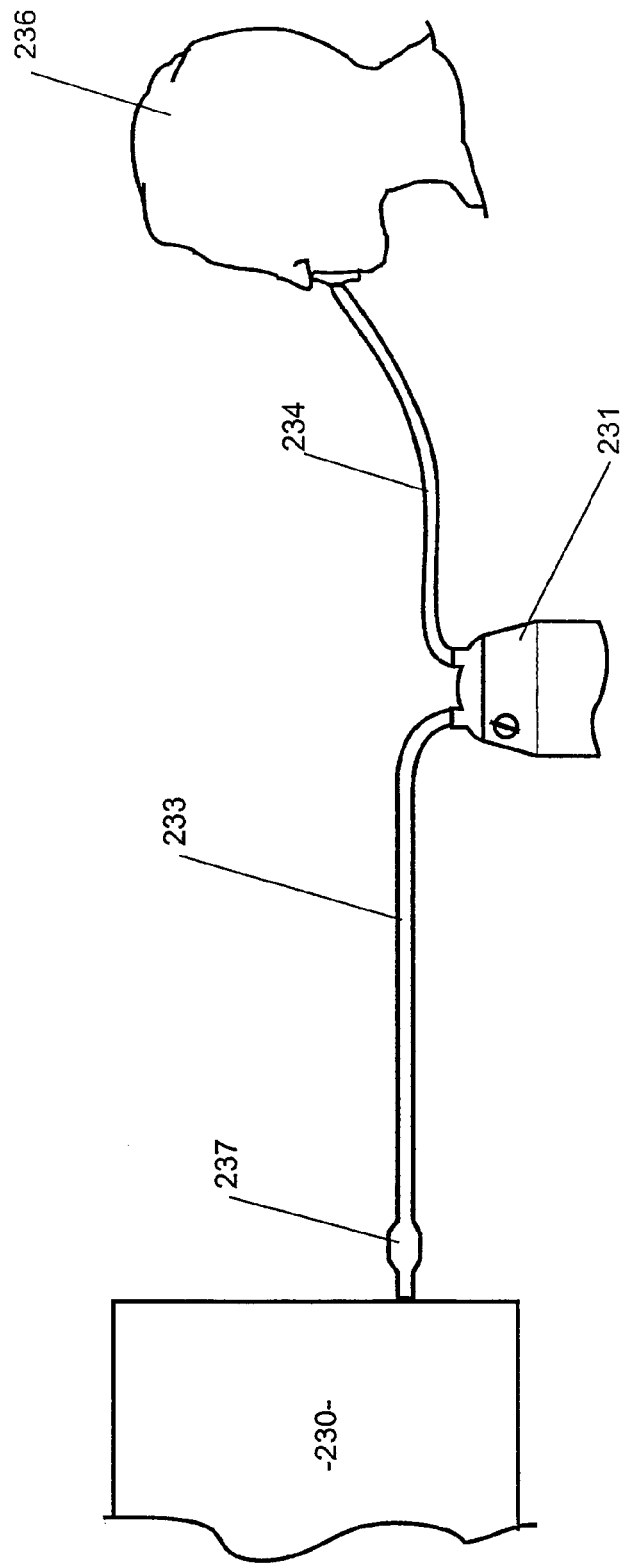
FIG. 6 is a block diagram of a typical breathing assistance apparatus circuit, according to the preferred embodiment of the present invention.

A typical pressure profile as might be experienced by a patient treated using the present invention is shown in FIG. 7. This illustrates the high pressure during inhalation 300, the point at which the valve vents the respirator output 301, and the relatively low pressure during exhalation 302. This compares with a typical pressure profile of a patient treated without the present invention shown in FIG. 6. This illustrates that the pressure experienced during exhalation 308 is similar to that during inhalation 306.

It will be appreciated from the above description that during exhalation the patient does not have to exert as much force to exhale as would normally be the case with traditional CPAP therapy. Thus the present invention provides a simple method of improving the quality of CPAP therapy without increasing the bulk of the apparatus worn by the patient.

Figure 9:
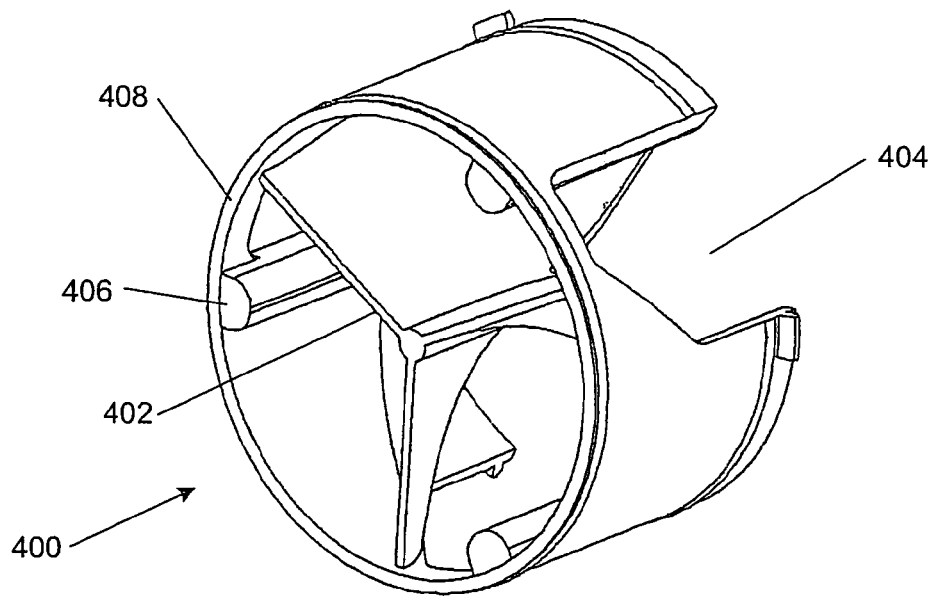
FIG. 9 is a perspective view of the valve member in another embodiment.
Figure 10:
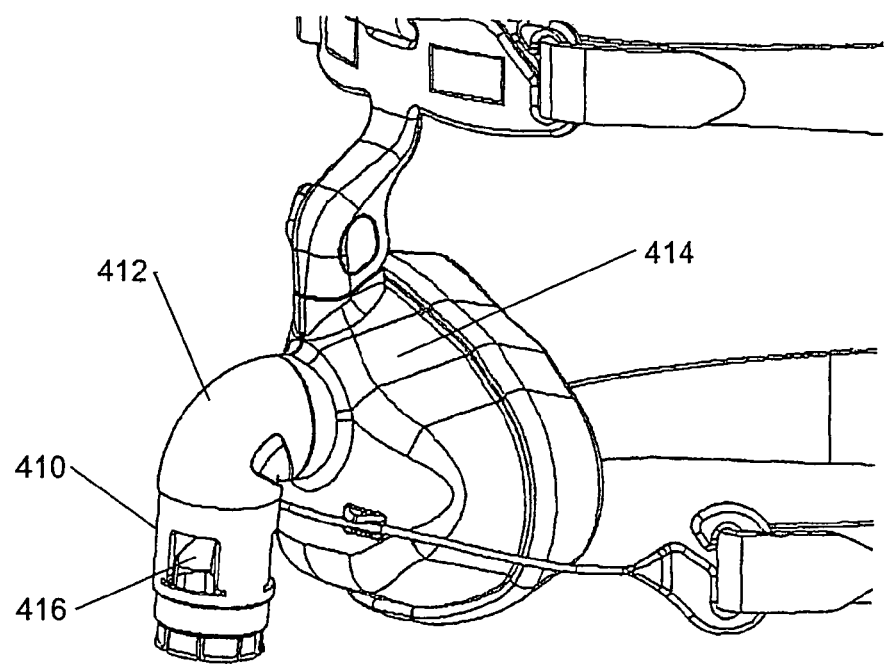
FIG. 10 is a perspective view of the valve member of the alternate in the other embodiment in use on a nasal mask.
Figure 11:
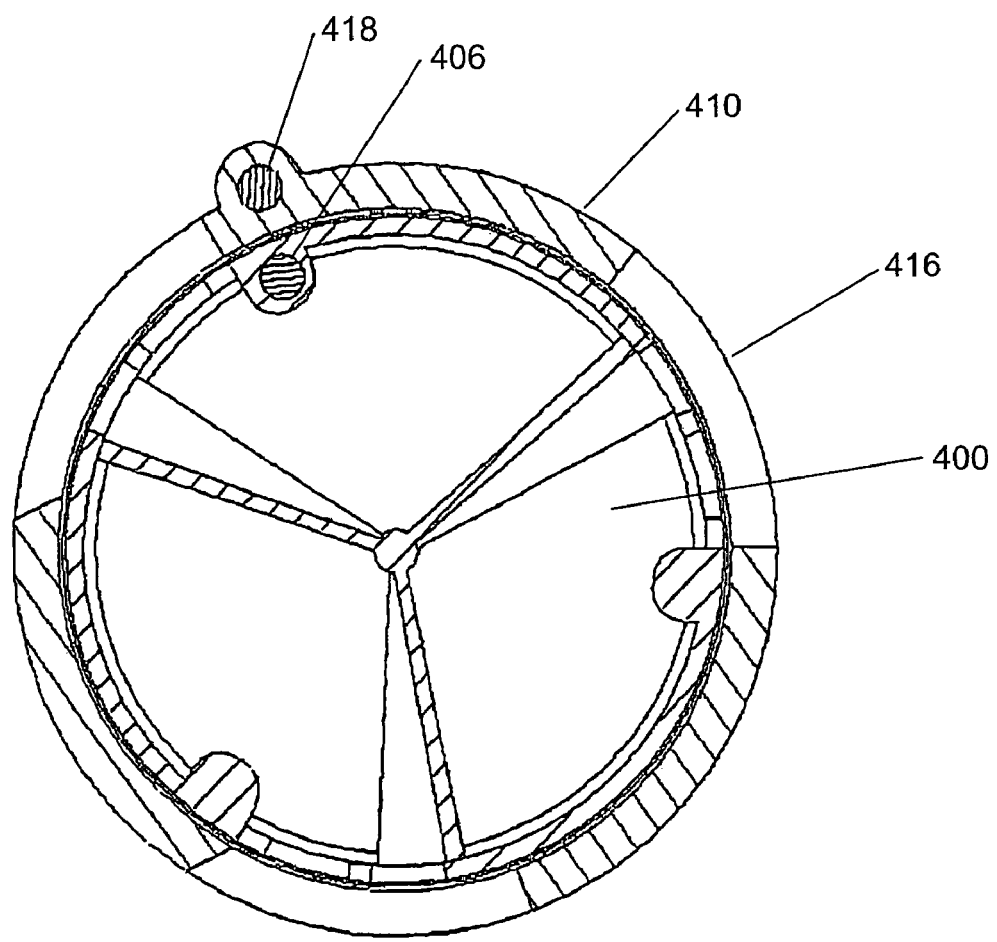
FIG. 11 is a cross section of the valve of the other embodiment.

In a second embodiment the present invention may be employed as an antiasplyxiation valve. Referring to FIGS. 9 to 11 the second embodiment is shown implemented in a nasal mask however it will be appreciated application in any breathing equipment may be appropriate.

In FIG. 9 the valve member 400 is shown with three angled valves 402 and three apertures 404. Cylindrical rare earth magnets 406 are located on the periphery 408 to bias the valve member 400 towards an open position. The valve member 400 is housed within body portion 410.

In FIG. 10 the Body portion 410 is shown engaged to an elbow connector 412 to the inlet of a nasal mask 414. It is shown in an open position (no flow) with outlets 416 matching with aperture 404.

In FIG. 11 the cross section shows the placement of valve magnets 406 relative to the body magnets 418 in the open position. Each one magnetised to attract towards the open position where the outlets 416 match up with apertures 404. Less preferably the magnets could be configured to repel away from the closed position.

Preferably each vane has an entry angle of 0° and an exit angle of 45°. Preferably the magnets are 1.5 mm diameter cylinders of 10 m length and 2000–4000gauss strength. Less preferably the magnets could be replaced with a 4 cm-g torque strength coil spring.

The invention claimed is:

1. A device for controlling gas flow between a pressurised gases supply and a user, comprising:
   a body portion including a first opening adapted to be in fluid communication with a pressurised gases supply, a second opening adapted to be in fluid communication with a user, and an interior fluidally communicating said first opening with said second opening
   at least one auxiliary outlet in said body portion, and
   a valve located in the body portion and configured to close said outlet when said gas flow through said interior is above a predetermined threshold, wherein the valve comprises a rotatably movable member having an axis of rotation parallel to the direction of gas flow between the first opening and the second opening.

2. A device for controlling gas flow as claimed in claim 1 wherein said valve configured to fluidically communicate said outlet with said first opening and said second opening when said gas flow is below said predetermined threshold.

3. A device for controlling gas flow as claimed in claim 1, wherein said moveable member includes at least one vane, said vane adapted to import a helical or rotational force on said moveable member accordingly to said gas flow, biasing means restraining said rotation and at least one aperture configured to fluidally communicate said outlet with said interior when said gas flow is below said threshold and configured to close said outlet when said gas flow is above said threshold.

4. A device for controlling gas flow as claimed in claim 3, wherein said biasing means and said vane are configured such that said threshold is between said gas flow during inhalation and said gas flow during exhalation of said user.

5. A devise for controlling the gas flow as claimed in claim 4, wherein said at least one vane comprises four angled vanes.

6. A device for controlling gas flow as claimed in claim 5 wherein said biasing means comprises a torsional spring connected between said moveable member and said body portion.

7. A device for controlling gas flow as claimed in claim 3, wherein said biasing means and said vane are configured such that said threshold is below said gas flow during inhalation and exhalation of said user.

8. A device for controlling gas flow as claimed in claim 7, wherein said at least one vane comprises three angled vanes.

9. A device for controlling gas flow as claimed in claim 8 wherein said biasing means comprise at least one magnet in said movable member or said body portion magnetically interacting with a magnetic material in said body portion or said moveable member respectively.

10. A system for supplying gases to a user at a pressure above ambient comprising:
    a pressurised gases supply,
    gases delivery means for supplying said gases to said user in fluid communication with said pressurised gases supply and said user, and
    flow control means disposed within said gases delivery means or in fluid communication therewith, said flow control means comprising a device according to any one of claims 1, 2 and 3–9.

11. A system as claimed in claim 10, wherein a system further comprising humidification means, for humidifying said gases before delivery to said user, is disposed within or fluid communication with said gases delivery means.

* * * * *